US00PP32405P2

(12) United States Plant Patent
van der Walt

(10) Patent No.: US PP32,405 P2
(45) Date of Patent: Oct. 27, 2020

(54) *TULBAGHIA* PLANT NAMED 'FLAMINGO'

(50) Latin Name: ***Tulbaghia* hybrid**
Varietal Denomination: Flamingo

(71) Applicant: Ivan van der Walt, Pretoria (ZA)

(72) Inventor: Ivan van der Walt, Pretoria (ZA)

( * ) Notice: Subject to any disclaimer, the term of this patent is extended or adjusted under 35 U.S.C. 154(b) by 0 days.

(21) Appl. No.: 16/501,682

(22) Filed: May 22, 2019

(51) Int. Cl.
*A01H 5/02* (2018.01)
*A01H 6/04* (2018.01)

(52) U.S. Cl.
USPC ..... Plt./263.1

(58) Field of Classification Search
USPC ..... Plt./263.1, 258
See application file for complete search history.

(56) References Cited

U.S. PATENT DOCUMENTS

PP27,404 P2 11/2016 van der Walt

*Primary Examiner* — Susan McCormick Ewoldt
*Assistant Examiner* — Karen M Redden
(74) *Attorney, Agent, or Firm* — Panitch Schwarze Belisario & Nadel LLP

(57) ABSTRACT

A new and distinct variety of *Tulbaghia* Plant, referred to by its cultivar name, 'Flamingo', is provided which forms attractive, pink-mauve colored flowers. Bright pink stem and leaf base color is exhibited. Light lime green colored foliage is formed with small pink tips. The vegetation is moderately vigorous and the growth habit is upright. The new variety is particularly well suited for providing distinctive ornamentation in the landscape.

3 Drawing Sheets

Figure 1:
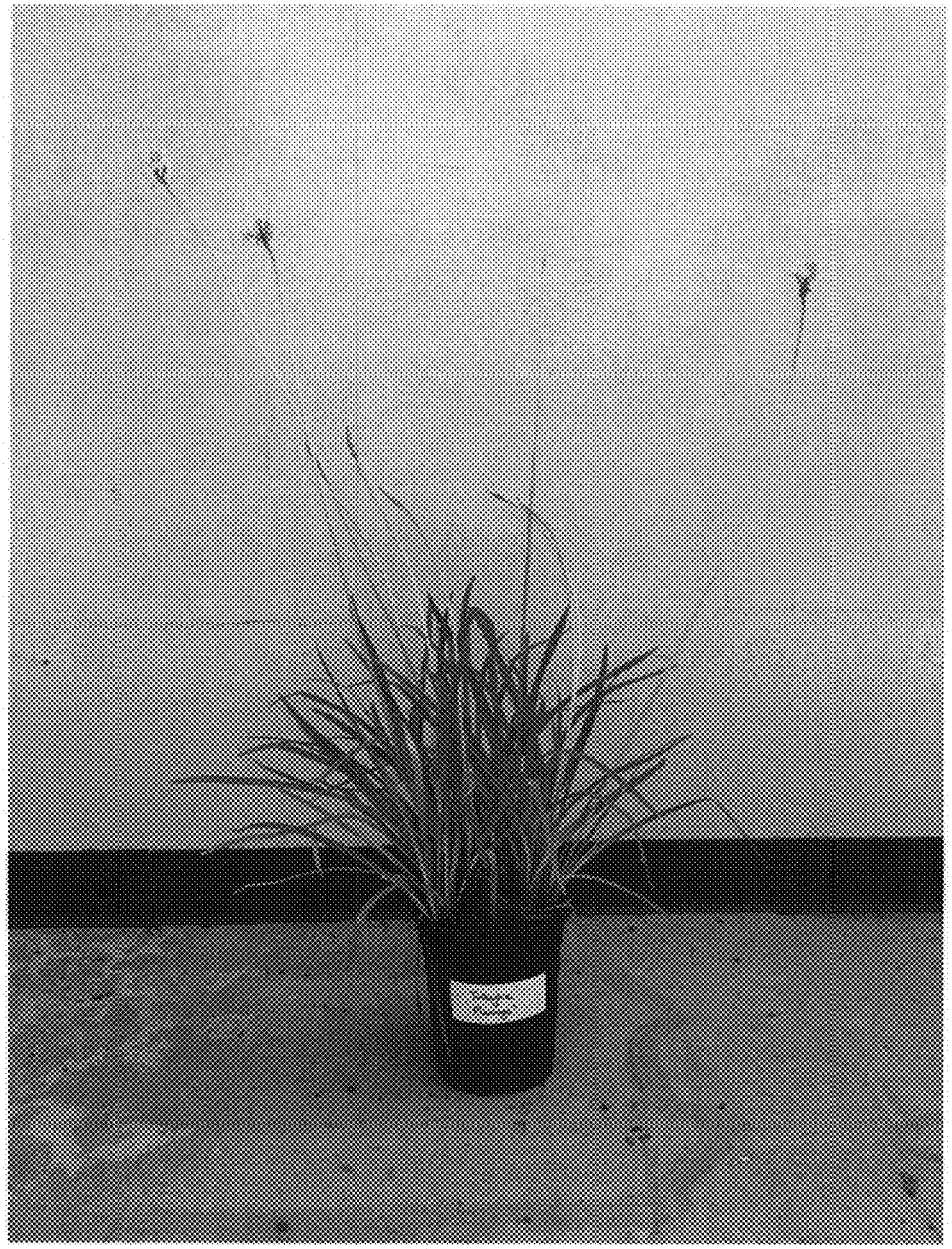

Botanical/commercial classification:
Latin name—*Tulbaghia* hybrid.
Varietal denomination: 'Flamingo'.

SUMMARY OF THE INVENTION

The new variety of *Tulbaghia* plant, botanically known as *Tulbaghia* hybrid, of the present invention was created in a controlled breeding program in Pretoria, Gauteng, South Africa during summer 2014. The objective of the breeding program was to produce a new ornamental cultivar of *Tulbaghia* for the horticultural industry.

The new *Tulbaghia* cultivar is the result of self-pollination. The female (seed) parent of the new cultivar is 'Kilimanjaro' (not patented in the U.S.). The male (pollen) parent of the new cultivar is 'Kilimanjaro' (not patented in the U.S.).

The parentage can be summarized as follows:

'Kilimanjaro' x 'Kilimanjaro'

The new cultivar was discovered and selected as a single flowering plant within the progeny of the above stated self-pollination during summer 2015 in a controlled environment in Pretoria, Gauteng, South Africa.

It was found that the new *Tulbaghia* Plant of the present invention possesses the following combination of characteristics:

(a) forms attractive pink-mauve colored flowers,
(b) exhibits bright pink stem and leaf base color,
(c) forms light lime green foliage with small pink tips,
(d) provides moderately vigorous vegetation, and
(e) forms an upright growth habit.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the parental variety, 'Kilimanjaro', displays dark green colored foliage and a stem and a flower bud color that is darker in coloration compared to the new variety. Moreover, the new variety can be readily distinguished from other similar non-parental varieties. For example, the 'Ashanti' variety (U.S. Plant Pat. No. 27,404) exhibits light pink colored flowers and medium-green colored foliage, whereas the new variety exhibits pink-mauve colored flower, and light lime green colored foliage with pink tips.

The new variety has been found to undergo asexual propagation in Pretoria, Gauteng, South Africa by division since summer 2016. Asexual propagation techniques in South Africa, such as division, have shown that the characteristics of the new variety are homogeneous, stable, and strictly transmissible by such asexual propagation from one generation to another. Accordingly, the new variety undergoes asexual propagation in a true-to-type manner.

The new variety has been named 'Flamingo'.

BRIEF DESCRIPTION OF THE PHOTOGRAPHS

The accompanying photographs show, as nearly true as it is reasonably possible to make the same in color illustrations of this character, typical specimens of the new variety. Colors in the photographs differ slightly from the color designations cited in the detailed description, which accurately describes the colors of the new variety. The illustrated plants of the new variety were approximately sixteen months of age and were observed at Arroyo Grande, Canada while growing in an outdoor nursery in one-gallon containers.

FIG. 1—illustrates a specimen of the plant—side view, displaying the overall growth and flowering habit.

Figure 2:
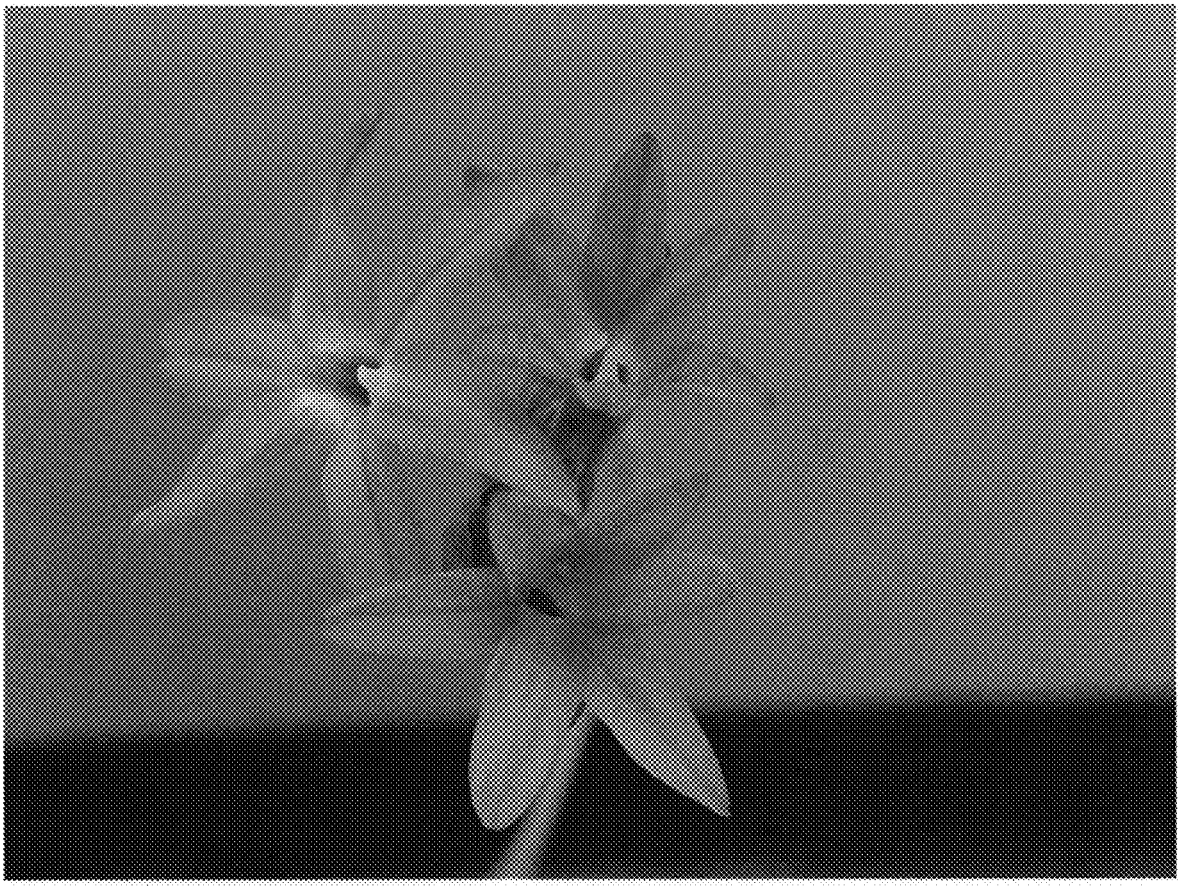

FIG. 2—illustrates a specimen of the flower—close-up view.

Figure 3:
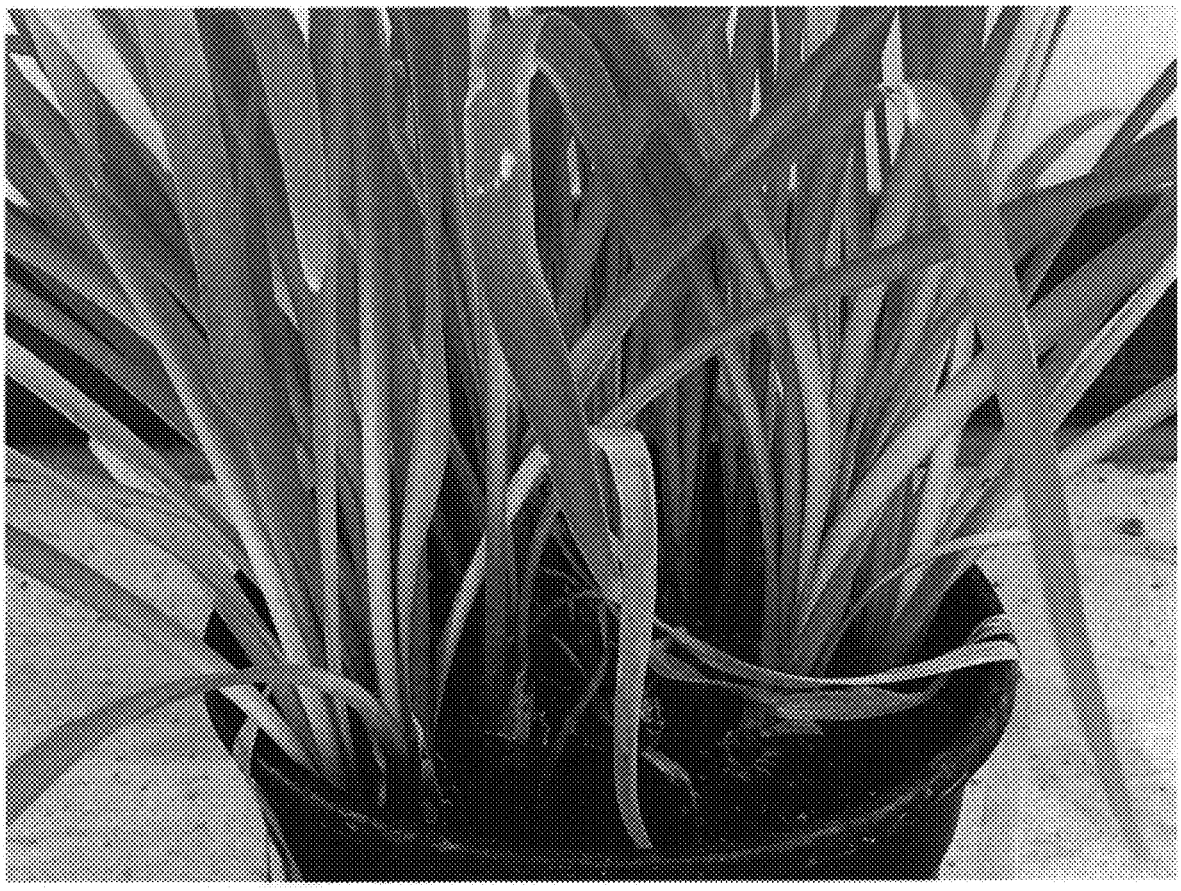

FIG. 3—illustrates a specimen of the foliage—close-up view.

DETAILED BOTANICAL DESCRIPTION

The chart used in the identification of colors is that of The Royal Horticultural Society (R.H.S. Colour Chart, 2015 edition), except where general color terms of ordinary significance are used. The terminology which precedes reference to the chart has been added to indicate the corresponding color in more common terms. The color values were determined in April 2019 under natural light conditions at Cochranville, Pa. The description, including measurements, is based on the observation of specimens of the new variety produced by division of stock plants and grown under outdoor nursery production conditions for approximately sixteen months in one-gallon containers utilizing a soilless growth medium. The specimens were then sent to Cochranville, Pa. and grown indoors for approximately one month. Measurements and numerical values represent averages of typical plants.

Class: *Tulbaghia* plant.

Propagation:

*Type*.—Division.

*Root description*.—Corm-like rhizome with thick roots.

*Root color*.—Commonly near Greyed-White Group 156C.

*Rooting habit*.—Freely branching.

Plant:

*Growth habit and general appearance*.—Moderately vigorous, upright-mounded, clumps of arching leaves and flowering stalks.

*Height*.—Approximately 67.0 cm on average from soil level to top of flowering scape; approximately 37.0 cm from soil level to top of foliage.

*Width*.—Approximately 45.0 cm on average.

*Branching habit*.—No branching, basal rosettes of leaves. — number of clumps per pot: approximately 2. — number of rosettes per clump: approximately 10.

Foliage:

*General*.—Quantity of leaves per rosette: approximately 8. — fragrance: strong garlic-scented when leaves bruised. — form: simple. — arrangement: 2-ranked.

*Leaves*.—Aspect: emerging leaves erect, then cascade. — shape: linear. — margin: entire. — apex: broadly acute. — base: sessile, sheathed. — venation pattern: parallel. — length of mature leaf: approximately 35.0 cm on average. — width of mature leaf: approximately 1.0 cm on average. — texture of upper and lower surfaces: glabrous. — color of upper surface of the top ¾ of young and mature foliage: commonly near Yellow-Green Group 144A with venation indistinguishable and near Red-Purple Group N74C at the leaf apex. — color of lower surface of the top ¾ of young and mature foliage: commonly a blend of near Yellow-Green Group 144A and Yellow-Green Group 144B with venation indistinguishable and near Red-Purple Group N74D at the leaf apex. — color of upper surface of the lower ¼ of young and mature foliage: commonly near Purple Group 75B with venation indistinguishable. — color of lower surface of the lower ¼ of young and mature foliage: commonly near Purple Group 75A with venation indistinguishable.

Inflorescence:

*General description*.—Type: umbel, semi-spherical; positioned above foliage. — quantity of fully open umbels per plant: approximately 1. — quantity of developing umbels per plant: approximately 3. — fragrance: strong garlic scent. — length or height: approximately 3.0 cm on average. — width: approximately 2.0 cm on average. — quantity of fully open flowers per inflorescence: approximately 1.

*Scape*.—Strength: strong. — shape in cross-section: round, slightly flattened. — aspect: erect to 45° angle. — length: approximately 62.0 cm on average. — diameter: approximately 4.0 mm on average. — texture: glabrous, glaucous. — color: closest to near Yellow-Green Group 150C transitioning to near Purple Group 75B near the scape base.

Flower:

*General description*.—Type: single, apetalous. — shape: salverform. — diameter: approximately 2.0 cm on average. — depth: approximately 2.0 cm on average.

*Bud rate of opening*.—Generally, takes 3 to 4 days for bud to progress from first color to fully open flower.

*Bud just before opening*.—Shape: obovate. — length: approximately 2.6 cm on average. — width: approximately 9.0 mm on average. — texture: glabrous, glaucous. — color: commonly near Purple-Violet Group N82B.

*Tepals*.—Quantity: 6 lobed in 2 slightly imbricate whorls. — shape: narrowly ovate. — appearance: dull. — margin: entire. — apex: acute. — base: fused. — length: approximately 1.3 cm on average. — width: approximately 5.0 mm on average. — texture of upper and lower surfaces: glabrous. — color of upper surface when first and fully open: commonly near Purple Group 76B with a line of near Purple Group 76A along the middle axis. — color of lower surface when first and fully open: commonly near Purple Group 76A.

*Perianth tube*.—Length: approximately 1.2 cm on average. — width: approximately 3.0 mm on average. — texture: glabrous. — color: commonly near Purple Group 76C and near Yellow-Green Group 144D where the base joins the pedicel.

*Pedicel*.—Strength: strong. — aspect: acute angle to horizontal. — length: approximately 1.0 cm on average. — diameter: approximately 1.0 mm on average. — texture: glabrous. — color: commonly near Purple Group 75A transitioning to near White Group 155A at the base.

*Reproductive organs*.—Androecium: quantity is 6 per flower, filaments adnate to perianth tube, anthers in 2 groups, upper group top of anther positioned 3.0 mm from tube opening and lower group top of anther positioned 5.0 mm from tube opening. — anther shape: oblong. — anther length: approximately 2.0 mm on average. — anther color: commonly near Yellow Group 12B. — pollen amount: moderate. — pollen color: commonly near Yellow Group 12B. — gynoecium: — pistil quantity: 1 per flower. — pistil length: approximately 1.0 mm on average. — stigma shape: capitate, papillate. — stigma length: less than 1.0 mm. — stigma color: colorless, translucent. — style length: less than 1.0 mm. — style color: commonly near Yellow-White Group 158C. — ovary length: approximately 1.5 mm on average. — ovary color: commonly near Yellow-Green Group N144B.

*Seed/fruit*.—None observed to date.

Development:

*Commercial crop time*.—Approximately 52 to 60 weeks from a division to finish in a one-gallon pot.

*Flowering habit*.—Freely flowering under outdoor growing conditions with substantially continuous blooming from spring through autumn.

*Lastingness of individual umbel on the plant*.—Approximately 2 to 3 weeks.

*Cold hardiness*.—To USDA Zone 7.

*Resistance to disease*.—Resistance to pathogens and pests common to *Tulbaghia* has not been observed.

Plants of the 'Flamingo' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Tulbaghia* Plant characterized by the following combination of characteristics:

(a) forms attractive pink-mauve colored flowers, (b) exhibits bright pink stem and leaf base color, (c) forms light lime green foliage with small pink tips, (d) provides moderately vigorous vegetation, and (e) forms an upright growth habit;

substantially as herein shown and described.

* * * * *